(12) United States Patent
Barnes

(10) Patent No.: US 11,076,871 B2
(45) Date of Patent: Aug. 3, 2021

(54) MULTIPLE CONNECTION DRIVE SHAFT

(71) Applicant: Medtronic PS Medical, Inc., Fort Worth, TX (US)

(72) Inventor: Milton F. Barnes, Fort Worth, TX (US)

(73) Assignee: Medtronic PS Medical, Inc., Fort Worth, TX (US)

( * ) Notice: Subject to any disclaimer, the term of this patent is extended or adjusted under 35 U.S.C. 154(b) by 551 days.

(21) Appl. No.: 15/252,858

(22) Filed: Aug. 31, 2016

(65) Prior Publication Data

US 2018/0055519 A1    Mar. 1, 2018

(51) Int. Cl.
| | | |
|---|---|---|
| *A61B 17/16* | (2006.01) |
| *B23B 31/107* | (2006.01) |
| *B25F 5/02* | (2006.01) |
| *B23B 31/20* | (2006.01) |

(52) U.S. Cl.
CPC ........ *A61B 17/1695* (2013.01); *A61B 17/162* (2013.01); *A61B 17/1631* (2013.01); *A61B 17/1688* (2013.01); *B23B 31/1071* (2013.01); *B23B 31/20* (2013.01); *B25F 5/02* (2013.01); *A61B 17/1628* (2013.01); *B23B 2231/2078* (2013.01)

(58) Field of Classification Search
CPC ... B23B 31/20; B23B 31/101; B23B 31/1071; A61B 17/162; A61B 17/1633; A61B 17/1613; A61B 17/1695
See application file for complete search history.

(56) References Cited

U.S. PATENT DOCUMENTS

| | | | |
|---|---|---|---|
| 2,878,701 A | | 3/1959 | Weersma |
| 4,441,563 A | * | 4/1984 | Walton, II ............ A61B 17/162 173/167 |
| 5,013,194 A | * | 5/1991 | Wienhold ........... B23B 31/1071 279/22 |
| 5,634,933 A | | 6/1997 | McCombs et al. |
| 5,741,263 A | * | 4/1998 | Umber ................. A61B 17/162 279/75 |
| 5,794,715 A | | 8/1998 | Norman |
| 5,888,200 A | * | 3/1999 | Walen ................ A61B 17/1622 606/167 |

(Continued)

FOREIGN PATENT DOCUMENTS

| | | |
|---|---|---|
| CN | 101743085 A | 6/2010 |
| CN | 103079756 A | 5/2013 |
| DE | 9214609 U1 | 12/1992 |

OTHER PUBLICATIONS

International Search Report and Written Opinion dated Feb. 12, 2018 in corresponding International Application No. PCT/US2017/049414.

(Continued)

*Primary Examiner* — Anna K Kinsaul
*Assistant Examiner* — Daniel Jeremy Leeds
(74) *Attorney, Agent, or Firm* — Harness, Dickey & Pierce, P.L.C.

(57) ABSTRACT

Disclosed is a system to engage a plurality of tools. In the system a drive shaft and collet may be assembled to engage and disengage, selectively, a plurality of tools. User selection may allow use of a plurality of tools during a procedure or during a plurality of procedures.

16 Claims, 11 Drawing Sheets

(56) References Cited

U.S. PATENT DOCUMENTS

| | | | | |
|---|---|---|---|---|
| 5,893,851 A * | 4/1999 | Umber | A61B 17/162 | 279/75 |
| 5,928,241 A * | 7/1999 | Menut | A61B 17/162 | 279/143 |
| 5,934,846 A * | 8/1999 | Ishii | B23B 31/008 | 279/22 |
| 6,045,564 A | 4/2000 | Walen | | |
| 6,562,055 B2 * | 5/2003 | Walen | A61B 17/1615 | 606/167 |
| 6,780,189 B2 * | 8/2004 | Tidwell | A61B 17/162 | 606/170 |
| 7,001,391 B2 * | 2/2006 | Estes | A61B 17/162 | 606/167 |
| 7,011,661 B2 * | 3/2006 | Riedel | A61B 17/162 | 606/170 |
| 7,066,940 B2 * | 6/2006 | Riedel | A61B 17/162 | 606/167 |
| 7,549,992 B2 * | 6/2009 | Shores | A61B 17/1633 | 606/79 |
| 7,559,927 B2 * | 7/2009 | Shores | A61B 17/162 | 606/79 |
| 7,669,860 B2 * | 3/2010 | Chiang | B23B 31/008 | 279/128 |
| 7,845,428 B2 * | 12/2010 | Sakamaki | B23B 31/1071 | 173/104 |
| 8,016,830 B2 * | 9/2011 | Veldman | A61B 17/7083 | 401/35 |
| 8,132,990 B2 * | 3/2012 | Bauman | B23B 31/008 | 408/239 R |
| 8,465,492 B2 * | 6/2013 | Estes | A61B 17/1615 | 606/82 |
| 8,529,567 B2 * | 9/2013 | Garcia | A61B 17/162 | 606/80 |
| 8,607,673 B2 * | 12/2013 | Marson | B25B 21/007 | 81/177.2 |
| 8,882,113 B2 * | 11/2014 | Porter | A61C 1/142 | 279/155 |
| 9,186,156 B2 * | 11/2015 | Xie | A61B 17/162 | |
| 9,414,848 B2 * | 8/2016 | Edwards | A61B 17/16 | |
| 9,504,478 B2 * | 11/2016 | Edwards | A61B 17/1624 | |
| 9,566,121 B2 * | 2/2017 | Staunton | F16D 1/116 | |
| 9,585,676 B1 * | 3/2017 | Russo | A61B 17/8875 | |
| 9,936,975 B2 * | 4/2018 | Siemer | A61B 17/62 | |
| 10,265,084 B2 * | 4/2019 | Ujvari | A61B 17/1617 | |
| 2004/0081523 A1 * | 4/2004 | Vasudeva | B23B 31/005 | 408/240 |
| 2004/0122460 A1 * | 6/2004 | Shores | A61B 17/162 | 606/180 |
| 2004/0155414 A1 * | 8/2004 | Baldwin | B23B 31/005 | 279/75 |
| 2004/0232631 A1 * | 11/2004 | Chen | B23B 31/1071 | 279/75 |
| 2008/0246233 A1 * | 10/2008 | Wienhold | B23B 31/1071 | 279/82 |
| 2009/0024129 A1 * | 1/2009 | Gordon | A61B 17/1617 | 606/80 |
| 2011/0196380 A1 * | 8/2011 | Cremer | A61B 17/162 | 606/104 |
| 2011/0260415 A1 * | 10/2011 | Lin | B23B 31/1071 | 279/43 |
| 2011/0301578 A1 | 12/2011 | Muniz-Medina et al. | | |
| 2012/0259337 A1 * | 10/2012 | del Rio | A61B 17/1615 | 606/80 |
| 2012/0283706 A1 * | 11/2012 | Blust | F16C 33/4605 | 606/1 |
| 2013/0245704 A1 * | 9/2013 | Koltz | A61B 17/00 | 606/86 A |
| 2015/0037111 A1 * | 2/2015 | Chang | B25B 15/001 | 408/202 |
| 2015/0327905 A1 * | 11/2015 | Barth | A61B 17/162 | 606/104 |
| 2016/0031017 A1 * | 2/2016 | Peters | B25B 23/0035 | 279/145 |
| 2017/0282257 A1 * | 10/2017 | Wang | B23B 31/1071 | |

OTHER PUBLICATIONS http://www.medtronic.com/us-en/healthcare-professionals/products/ear-nose-throat/powered-ent-instruments.html accessed Jun. 9, 2016.

International Preliminary Report on Patentability dated Mar. 14, 2019 in corresponding International Application No. PCT/US2017/049414.

Office Action regarding Chinese Patent Application No. 201780067190.0, dated Apr. 24, 2020.

Third Office Action regarding Chinese Patent Appication No. 201780067190.0, dated Apr. 15, 2021.

* cited by examiner

MULTIPLE CONNECTION DRIVE SHAFT

FIELD

The present disclosure relates to a drive shaft for a motor assembly, and particularly to a drive shaft configured to drive multiple tools.

BACKGROUND

During selected procedures, a motor may be provided to power a tool, such as a tool that has a tool tip or working end that is able to be powered in a selected manner. For example, the tool may be rotated at a selected velocity, such as about 100 rotations per minute (RPM) to about 80,000 RPMs. The tool interconnected with the motor may be connected to a drive shaft configured to be powered by the motor to rotate. A procedure may then be carried out with the tool tip while rotating when powered by the motor.

The motor may be selected to interconnect with a plurality of different types of tools. The various tools may be provided for different procedures, such as drilling a hole, inserting or fastening a fastener, milling a structure, or the like. Different tools may include different configurations, such as diameters, connection shapes, or the like. Accordingly, attachments may be provided to interconnect the drive shaft of the motor with different ones of the tools. The motor drive shaft, therefore, may not accommodate all tools that are selected to be driven by the motor assembly.

SUMMARY

This section provides a general summary of the disclosure, and is not a comprehensive disclosure of its full scope or all of its features.

A drive shaft includes a tool engaging portion to hold a tool within a drive shaft. The drive shaft may be included with a collet assembly. The drive shaft may include a plurality of driving regions to drive different tools of different sizes, including different diameters by the single drive shaft. Further, the drive shaft may include an axial fixation engaging portion to engage all different tools to axially fix the tools within the drive shaft. The axial fixation portion may include moveable members. The moveable members may be biased to an engaged configuration to engage the tools. The biasing mechanism may be moved to disengage the tool from the biased configuration. Therefore, a drive shaft assembly may be used to engage and drive different tools of different diameters without providing attachments or augments to engage differently sized tools.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
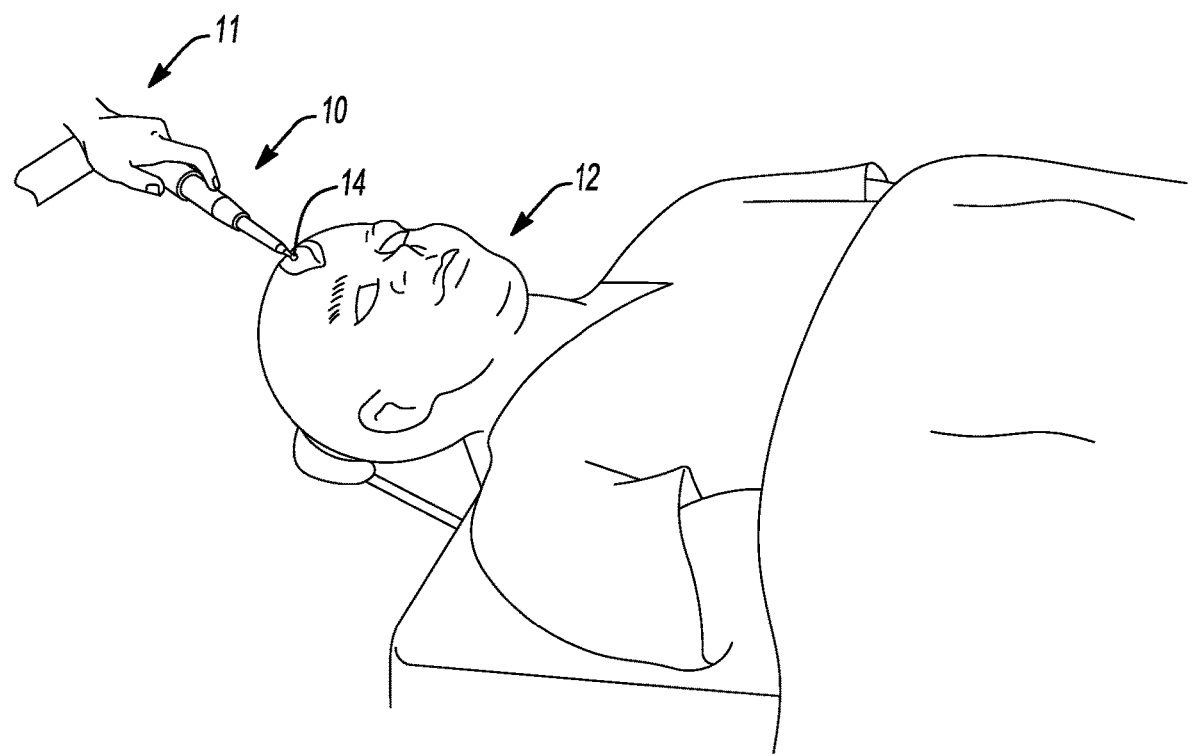
FIG. 1 is an environment view of a motorized assembly.

FIG. 1 is an environmental view of a motorized assembly 10 being used to perform a procedure on a subject 12. In various embodiments, the motorized assembly 10 may include a powered dissection tool for performing a select procedure, such as forming a burr hole in a cranium 14 of the patient 12. It is understood, however, that the instrument assembly 10 may be used for performing other procedures such as a removal of material relative to a nasal cavity of the subject 12 or other appropriate procedure. Further, it is understood that the motorized assembly 10 may be used to perform a procedure on a non-living subject such as powering a tool to drill a hole in an airframe, an automotive frame, or the like. Accordingly, the motorized assembly 10 is not required to be used with a living subject, such as a human patient.

Figure 2:
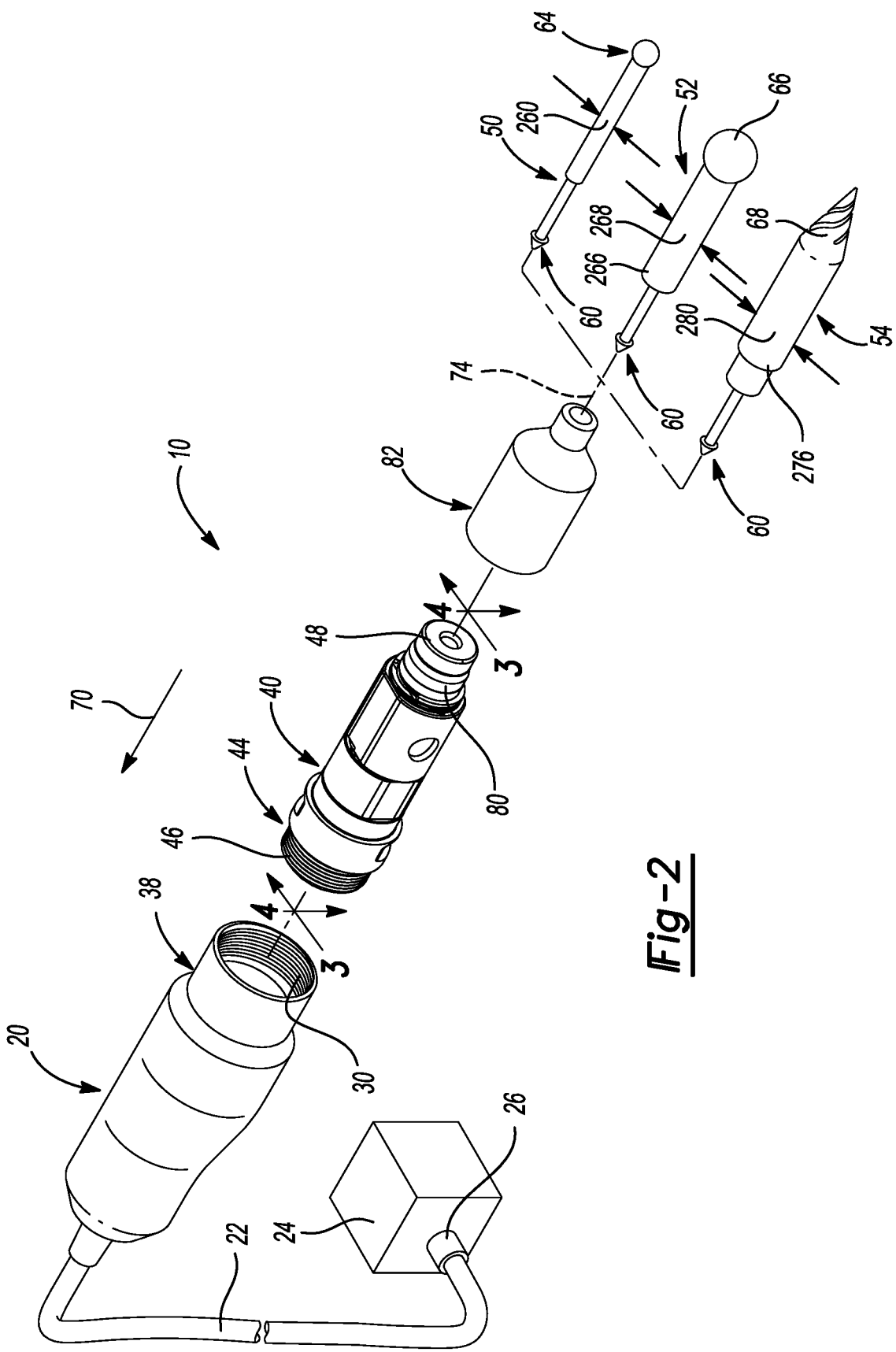
FIG. 2 is an exploded view of the motorized assembly.

With additional reference to FIG. 2 the motorized assembly 10 may include various components which may include a motor assembly or component 20. The motor component 20 may include an appropriate motor component such as the LEGEND EHS STYLUS® motors, sold by Medtronic, Inc. The motor component 20 may be electrically powered, such as the LEGEND EHS STYLUS® motors. The power may be provided to the motor assembly 20 via a tube 22 that is connected with a power source 24 via a connector 26. The power source may be any appropriate power source such as the IPC® integrated power system, sold by Medtronic, Inc. It is understood, however, that the motor component 20 may be any appropriate motor assembly such as one powered by pneumatic power, or other appropriate power supply. Therefore, a pneumatic or electric power drill is not intended to limit the subject disclosure or the pending claims. Moreover, the motor component 20 may include those disclosed in U.S. Pat. No. 7,011,661 or 7,001,391, both incorporated herein by reference.

The motor component 20 may include a connector 38 that has a threaded portion 30. The threaded portion 30 may threadably engage a collet and drive shaft assembly 40. The collet and drive shaft assembly 40 may also be referred to as a drive shaft assembly 40 and may include both a collet portion and a drive shaft. The drive shaft, as discussed herein, may be formed of one unitary piece or formed of a plurality of pieces that are connected. The drive shaft may engage a tool to move the tool for performing a procedure.

The drive shaft assembly 40 may include a motor connector or engaging portion 44 having external threads 46 to engage the internal threads of the threaded portion 30 of the connector 38 of the motor component 20. Accordingly, the drive shaft assembly 40 may be operably connected to the motor component 20 to power the drive shaft in the drive shaft assembly 40. The drive shaft assembly 40 may further include a tool receiving end 48. The tool receiving end 48, as discussed further herein, can receive one or more tools or tool tips such as a first tool tip 50, a second tool tip 52 and a third tool tip 54 from a kit of tools. An attachment 82 may also be received on the tool receiving end 48. The tools 50, 52, or 54 may selectively be placed through the attachment 82, if selected. Further, the kit may also include at least one additional of the drive shaft assembly 40, the motor component 20, and the attachment 82 along with the tools 50, 52, 54.

Each of the tool tips, including the first tool tip 50, the second tool tip 52, and the third tool tip 54 may include a tool or shaft retaining region 60 that may be substantially identical for each of the tool tips 50, 52, 54. Each of the tool tips may also include respective working ends such as a first working end 64, a second working end 66, and a third working end 68. Each of the working ends may be a similar type of working end or a different type of working end. For example, the first working end 54 may include a burr, the second working end 66 may include a mill, and the third working end 68 may include a fluted drill tip. The working ends may also be distal or terminal ends of the tools 50, 52, 54.

Nevertheless, each of the tool tips 50, 52, and 54 may be axially engaged within the drive shaft assembly 40 by moving the tool tip generally in the direction of the arrow 70. Once engaged in the drive shaft assembly 40, as discussed further herein, each of the tool tips 50, 52, and 54 may be axially retained within the drive shaft assembly 40. At least a portion of the drive shaft assembly 40, however, may rotate by being powered by the motor component 20 to also rotate the respective tool tips 50, 52 and 54 around an axis 74.

The drive shaft assembly 40 may include an attachment connection portion 80. The attachment connection portion 80 may allow a connection of the attachment 82. The attachment 82 may include a surface and/or bearing portion that assists in supporting one or more of the tools 50, 52, and 54. The attachment 82 may not be required to be connected to the drive shaft assembly 40, but may be selected for various tool portions. Further, the attachment 82 may include various additional features, such as allowing for an angled connection of the tool 50, 52, 54 to the drive shaft assembly 40.

Figure 3:
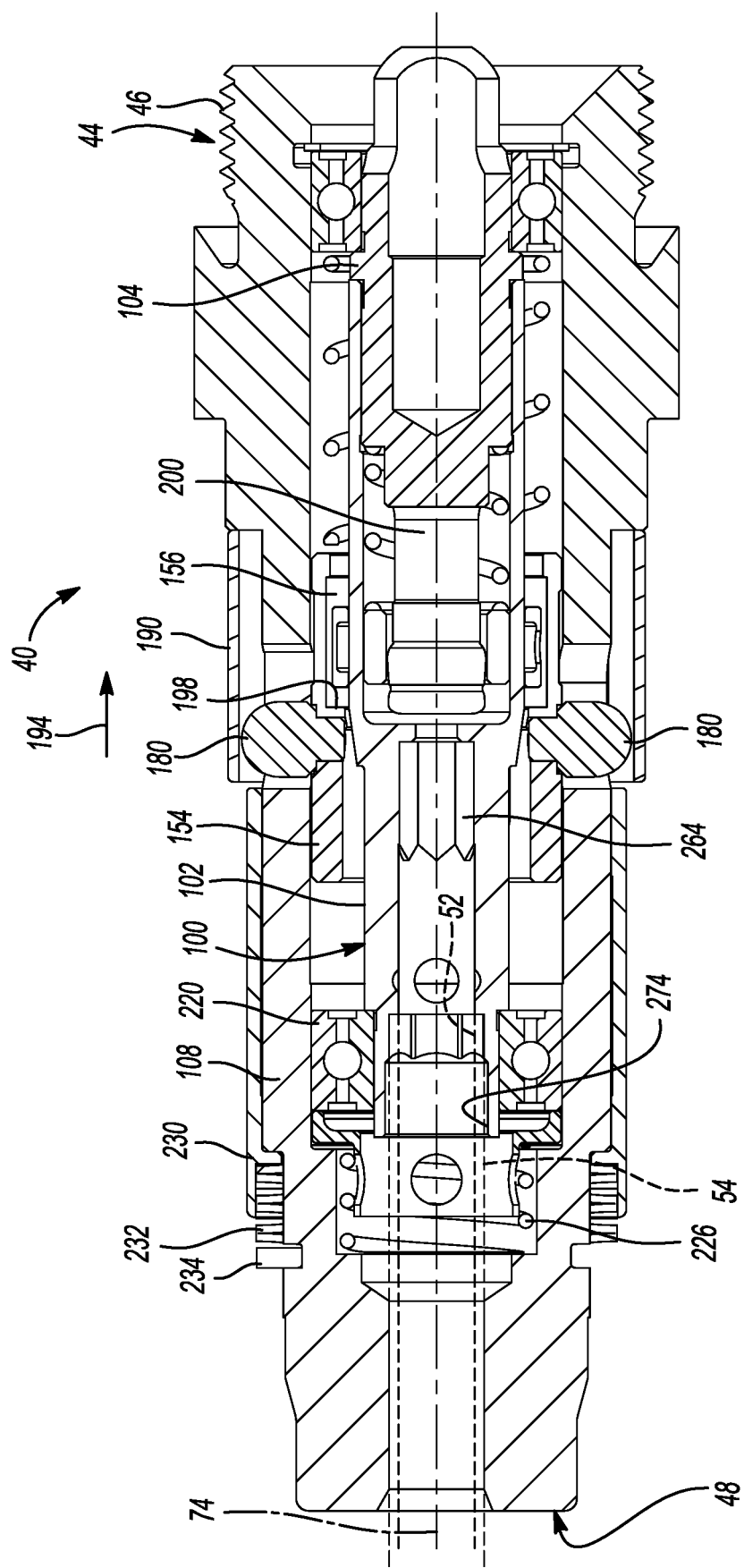
FIG. 3 is a cross-sectional view along line 3-3 of the collet and drive shaft assembly.
Figure 4:
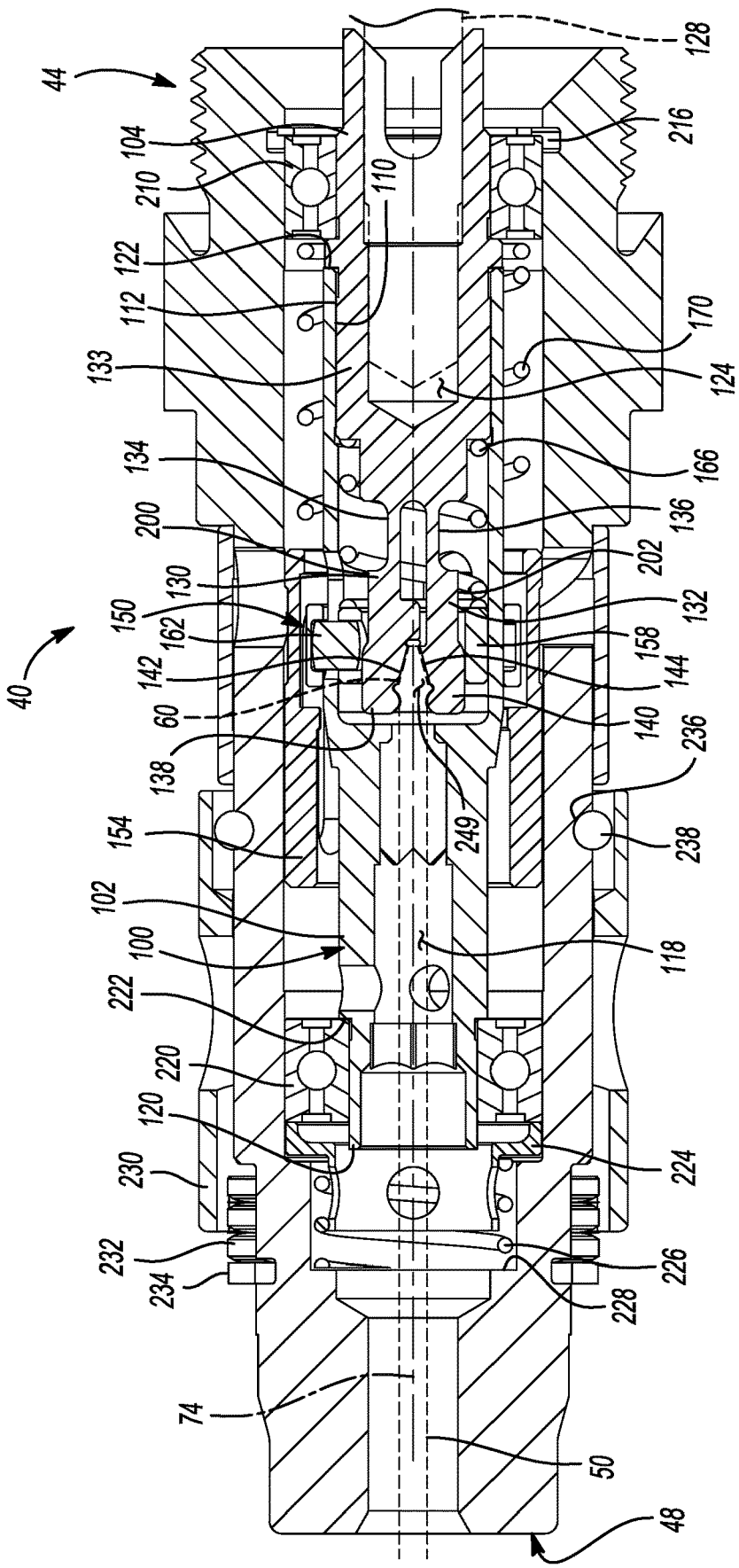
FIG. 4 is a cross-sectional view along line 4-4 of the collet and drive shaft assembly.
Figure 5:
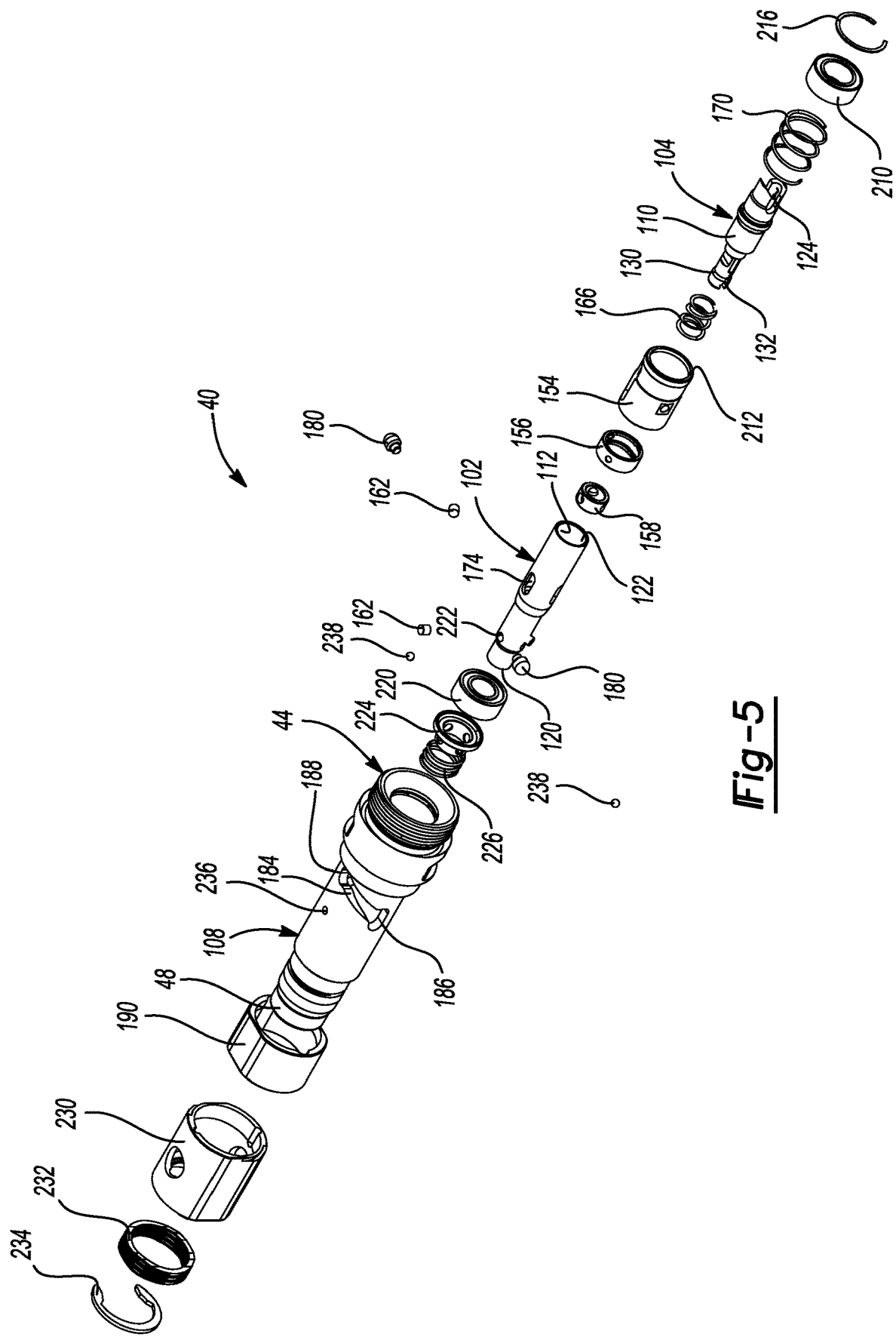
FIG. 5 is an exploded view of the collet and drive shaft assembly.

In reference to FIGS. 3, 4, and 5, the drive shaft assembly 40 may include a drive shaft 100 including a first drive shaft portion or member 102 and a second drive shaft portion or member 104. The drive shaft 100, however, may be formed of more than two pieces. The drive shaft 100 may be fit within a collet housing 108. The collet housing 108 may include the motor connector portion 44 including the external thread 46. The collet housing 108, therefore, may be attached to the motor component 20 via threading the external threads 46 to the internal threads 30.

Once the collet housing 108 is threaded to the motor assembly 20 the drive shaft assembly 40 may be powered with the motor assembly 20. It is understood, however, that the collet housing 108 may be fixed to the motor assembly 20 with other appropriate connection mechanisms. For example, a bayonet connection, a quarter turn connection, or other appropriate connections may allow the drive shaft assembly 40 to be removably attached to the motor assembly 20 via the connector 38. As discussed herein, the drive shaft 100 may then rotate relative to the collet housing 108 to rotate the tools 50, 52, 54.

The drive shaft 100 may be press fit together. For example, the second drive shaft portion 104 may include a first region 110 that has an external diameter that forms an interference fit with a connection region 112 of the first drive shaft portion 102. The connection region 112 may be formed within at least a portion of a throughbore 118 formed in the first shaft portion 102. The drive shaft 100 may, therefore, be assembled by press fitting the second drive shaft portion 104 into the portion of the bore 118 that forms the shaft connection portion 112. It is also understood, however, that the second drive shaft portion 104 may be fixed to the first drive shaft portion 102 in any appropriate manner such as by threading, welding, adhesives, brazing, or the like.

The first drive shaft portion 102 further includes the throughbore 118 that extends from a first end 120 to a second end 122 of the first drive shaft portion 102. The throughbore 118, as discussed further herein, allows for passing of the tools 50, 52, 54 into the first drive shaft portion 102 and further for assembling the second drive shaft portion 104 into the drive shaft connection portion 112 to form the drive shaft 100.

The second drive shaft portion 104 further includes a motor shaft receiving bore 124. The motor shaft receiving bore 124 may receive a motor shaft 128 (illustrated in phantom). The motor shaft 128 may interfere with an internal wall of the second shaft portion 104 that defines the internal bore 124 to allow for rotation of the first drive shaft portion 104. It is understood, however, that the motor shaft connection may include an external surface connection to the motor shaft 128, as well or in the alternative. Due to the interference fit of the connection portions 110 and 112, rotation of the second drive shaft portion 104 rotates the first drive shaft portion 102. As discussed further herein the rotation of the second drive shaft portion 104 and/or the first drive shaft portion 102 causes rotation of one or more of the tools 50, 52, and 54.

Further, the second drive shaft portion 104 includes two or more tangs or fingers including a first tang or finger 130 and a second tang or finger 132 that extend from a body portion 133. Each of the tangs 130, 132 may include spring or flex regions 134 and 136, respectively. The spring regions 134, 136 allow tool engaging regions 138, 140, respectively, to flex radially outward or inward to move relative to the body portion 133 to engage the tool retaining region 60 (shown in phantom in FIGS. 3 and 4). The tool engaging regions 138, 140 may include a selected or keyed geometry, such as an elongated surfaces 142, 144, respectively, to engage the tool retaining region 60. It is understood, however, that appropriate shapes may include a split hex shape, split square shape, or other appropriate shapes to transfer rotational force from the second drive shaft portion 104 to the tool retaining region 60. Further, the keyed shape of the surfaces 142, 144 may engage the tool retaining region 60 of the tools 50, 52, 54 to axially hold the tools within the drive shaft 100. Accordingly, the tool engaging regions 138, 140 may be moved towards the central axis 74 of the drive shaft assembly 40 to engage the tools 50, 52, 54.

The tangs 130, 132, particularly the tool engaging regions 138, 140 may be biased towards the central axis 74 by a biasing assembly 150. The biasing assembly 150 may include a carrier 154, an outer sleeve 156, an inner sleeve 158, one or more biasing pins 162, a first biasing spring 166 and a second biasing spring 170. In combination, the biasing assembly 150 allows for engagement and disengagement of the tool engaging regions 138, 140 with the tool retaining region 60.

The inner sleeve 158 and the biasing spring 166 may be positioned within the inner bore 118 of the first drive shaft portion 102. The assembly of the inner sleeve 158 and the first biasing spring 166 may occur prior to press fitting the second drive shaft portion 104 into the bore 118 to form the connection between the connection regions 110, 112. The inner sleeve 158 may, optionally, be retained at within the bore 118 at least partially with a shoulder formed in the first shaft portion 102.

The biasing pins 162 may be placed through one or more bores 174 formed through the first drive shaft portion 102. The outer sleeve 156 may be placed over the biasing pins 162 to capture the biasing pins 162 between the inner sleeve 158 and the outer sleeve 156. The pins 162 may be passed through the bores 174 that are formed as elongated slots in the first drive shaft portion 102. The elongated slots 174 allow movement of the inner sleeve 158, the outer sleeve 156, and the biasing pins 162 along the axis 74. The first biasing spring 166, however, generally provides a biasing force to bias the inner and outer sleeves, 158, 156 and pins 162 generally towards the tool receiving end 48 of the drive shaft assembly 40.

When the first biasing spring 166 biases the inner sleeve 158 towards the tool receiving end 48, the tool engaging regions 138, 140 are compressed towards the central axis 74 and may engage the tool retaining region 60. Therefore, the tool is held axially relative to the drive shaft 100. During operation, such as in inserting or removing a selected tool from the drive shaft 100, the drive shaft assembly 40 may be manipulated to unbias and/or rebias the tool engaging regions 138, 140 to engage the tool retaining region 60. In particular, the carrier 154 may be engaged by carrier pins 180. It is understood that an appropriate number of carrier pins 180 may be provided, and two are illustrated merely for illustration. Each of the carrier pins 180 may extend through the collet housing 108 through grooves, such as J-grooves 184. The J-grooves 184 may extend from a first end 186 that is nearer to the tool receiving end 48 to a second end 188 that is further away from the tool receiving end 48 than the first end 186.

A first ring 190 may rotate relative to the collet housing 108. The carrier pins 180, upon rotation of the ring 190, may move towards to the motor connector portion 44 of the collet housing 108, generally in the direction of arrow 194. As the pins move in the J-groove 184, the pins 180 move the carrier 154 also in the direction of arrow 194. As the carrier 154 moves in the direction of arrow 194, a shoulder 198 engages the outer sleeve 156 to also move the outer sleeve in the direction the arrow 194. As discussed above, the outer sleeve captures the biasing pins 162 relative to the inner sleeve 158. Therefore, movement of the outer sleeve 156 moves the biasing pins 162 and the inner sleeve 158 also in the direction of arrow 194. As the biasing pins 162 move in the direction of the arrow 194, the biasing pins 162 move away from the tool engaging region 138, 140 of the tangs 130, 132 to a narrowed region 200 and 202 of the respective tangs 130, 132. Therefore, as the biasing pins 162 move to the narrowed regions 200, 202 the spring portions 134, 136 allow the tool engaging regions 138, 140 to move away from the central axis 74. In this way, the respective tool 50, 52, 54 may be disengaged from the tool retaining region 60 and may be moved axially out of the collet housing 108. Once the tool is removed and either a new tool is inserted or the procedure may be completed, the ring 190 may be twisted to move the carrier pins 180 in the direction opposite the arrow 194. Further, the second biasing spring 170 may assist in biasing the carrier 154 generally towards the tool receiving end 48 away from the motor engaging portion 44. Therefore, the second biasing spring 170 may provide a biasing force, in addition to the biasing force provided by the first biasing spring 166, to assist in biasing the tool engaging portions 138, 140 towards an engagement or closed position relative to the tool retaining region 60 of the inserted tool to assist in holding the tool 50, 52, 54 in the tool drive shaft 100.

The second biasing spring 170 may be held between a first drive shaft bearing 210 and an end 212 of the carrier 154. The bearing 210 may allow rotation of the drive shaft 100 and bear on the second shaft portion 104 near the motor connector portion 44. The bearing 210 may be held within the collet housing 108 with a snap ring or fixation ring 216. It is understood, however, any appropriate fixation or holding member may be used to hold the bearing 210 in the collet housing 108 and the snap ring 216 is merely exemplary. Further, compression of the motor component 20 on the drive shaft assembly 40 may assist or form a force to hold the bearing 210 in place.

Within the collet housing 108 may be placed a second drive shaft bearing 220 to bear or hold the first drive shaft member 102 axially and radially within the collet housing 108. The bearing 220 may also bear on the first shaft portion 102 during rotation. The bearing 220 may be held within the collet housing 108 against a shoulder 222 of the first drive shaft portion 102 and a spacer 224. The spacer 224 may be biased against the bearing 220 with a third biasing spring 226 that is held against a shoulder or wall surface 228 of the collet housing 108.

The drive shaft assembly 40 may further include a second ring 230, a wave spring 232, and a C-clip 234. The C-clip 234 may assist in holding the wave spring 232 onto the collet housing 108. Further, one or more locking balls 238 may assist in fixing the second sleeve 230 rotationally relative to the collet housing 108 by being received within indents 236 in the collet housing 108. The second ring 230 may be moved axially along the axis 74 to assist in engaging the attachment 82 onto the collet housing 108. Further, the wave spring 232 may further assist in biasing and holding the attachment 82 relative to the collet housing 108.

Accordingly, the drive shaft assembly 40 may include the drive shaft 100 that may be powered by the motor component 20 to rotate tools, such as the tools 50, 52, 54 relative to the collet housing 108. The drive shaft 100 may include a plurality of tool driving regions or portions to allow transfer of rotational force to the respective tools. Different tool driving regions may engage differently sized tools.

As illustrated in FIG. 3, the tool retaining region 60 of the tool 50 may be received and engaged substantially only at the tool engaging regions 138, 140. Therefore, the keyed portion of the tool engaging portions 138, 140 may form a first tool driving region 249. The tool 50 may include a diameter 260 that is about 1.0 millimeters (mm) to about 1.3 mm in diameter. Therefore, an exterior surface of the tool 50 may not contact any other portion of the first drive portion 102 when inserted into the drive shaft 100 and engaged in the first tool driving region 249. The tool retaining region 60 may be the only portion engaged within the drive shaft 100 to hold the tool 50 within the drive shaft 100 and to transfer rotational forces to the tool 50.

The first tool driving region 249 may be used to transfer rotational forces, including torque, to the tool 50 and/or the other tools 52 and 54. The first tool driving region 249 may also operate, as discussed herein, to axially fix all of the tools 50, 52, and 54 within the drive shaft 100. Therefore, the first tool driving region 249 may operate as both a rotational driver and an axial fixation mechanism. In operation with various tools, as discussed herein, the first tool driving region 249 may operate substantially or only as an axial fixation mechanism.

The first tool portion may include a second tool driving region 264. The second tool driving region 264 may include a selected geometry, such as a hex shape. Other appropriate geometries, however, may also be provided such as square, triangular, or the like. The second tool driving region 264 may engage a tool drive region 266 on the tool 52. The tool 52 may include a second diameter 268 that is greater than the diameter 260 and allows for the drive region 266 to engage the second tool driving region 264 of the first drive shaft portion 102. The diameter 268 may be about 2.0 mm to about 2.5 mm. The tool 52 may also, as discussed further herein, include the retaining region to engage the first tool driving region 249. The first tool driving region 249 may operate, however, to substantially or only axially fix the tool 52 within the drive shaft 100.

The first drive portion 102 may further include a third tool driving region 274. The third tool driving region 274 may, for example, be hexagonal in shape or may include other appropriate shapes such as a square, triangle, or the like. The third tool 54 may further include the tool retaining region 60 that may be received in the tool engaging regions 138, 140 of the tangs 130, 132 and also a drive region 276 that may be complementary to and be received within the third tool driving region 274. The third tool 54 may include a third diameter 280 that may be different, such as greater than, both the first diameter 260 and the second diameter 268. The diameter 280 may be about 3 mm to about 3.2 mm. Again, the first tool driving region 249 may operate to substantially or only axially retain the tool 54 within the drive shaft 100.

Accordingly, regardless of the diameter 260, 268, or 280 of the tools 50, 52, 54, respectively, each may be driven by the tool drive shaft 100. Therefore, the tool drive shaft 100 including at least the first, second, and third tool driving regions 249, 264, and 274 may engage at least three different sizes of tools. As discussed above, each of the tools may have different sizes or different diameters, including the respective diameters 260, 268, 280, and may be provided for varying and different purposes.

It is understood, however, that the tool drive shaft 100 may include various numbers of tool driving regions. In various embodiments, at least one of the tool driving regions may be variable or moveable, such as the tool driving region 249 formed by the tangs 130, 132. In other words, the tangs 130, 132 may move to engage or disengage one or more tools. Further, one or more of the tool driving regions may have fixed dimensions. For example, the tool driving region 264 may have a fixed geometry to engage a selected tool. Still further, a selected tool may engage more than one of the tool driving regions. Also, the driving regions, such as the driving regions 249, 264, and 274 may be separate and spaced apart from one antoer. For example, as illustrated in FIG. 3, each of the driving regions 249, 264, and 274 are spaced apart from one another along the axis 74.

With reference to FIGS. 1 through 4, during an operative procedure a user 11 may be provided with a kit or system, such as illustrated in FIG. 2, which may include at least the three tools 50, 52, 54 either selected by a user, such as a predetermined selection, or provided as a kit of more than the three tools 50, 52, 54. The kit may further include the attachment 82 and other appropriate portions selected by the user. During a procedure, such as an operative procedure, the user 11 may select to engage and disengage one or more of the tools 50, 52, 54 (or other tools) at different times during the procedure. For example the user 11 may first form a burr hole in the subject 12 and further form a milled portion of bone on the subject 12. The user 11 may first select to place the tool 50 in the tool drive shaft 100 for performing a first part of a procedure. The user 11 may then remove the first tool 50 and then place the second tool 52 in the tool drive shaft 100 for a further performance of the procedure. The tool drive shaft 100 including at least the three driving regions 249, 264, and 274 may allow for interconnection for all of the tools 50, 52, 54 with the tool drive shaft 100 that is a single drive shaft within the drive shaft assembly 40 without requiring or using additional attachments or portions to be connected to the drive shaft assembly 40, including the tool drive shaft 100.

The tangs 130, 132 may all be used to engage the tool retaining region 60 to axially hold, individually, all of the tools 50, 52, 54 within the tool drive shaft 100. As discussed above, the tool engaging regions 138, 140 of the tangs 130, 132 may be engaged to each of the tools 50, 52, and 54. Thus, the tool engaging regions 138, 140 of the tangs 130, 132 may axially fix and retain each of the tools 50, 52, 54. Therefore, the tool drive shaft 100 may both axially retain and rotationally drive each and all of the respective tools 50, 52, 54. Operation of the motorized assembly 10, therefore, may be used during an operative procedure according to a selected purpose including selecting and engaging one or more of the tools 50, 52, 54.

Further, it is understood that even though only a single tool may be used during an operative procedure, the tool drive shaft 100 may allow for interconnection of a plurality of tools with the single tool drive shaft 100 at a selected time. Moreover, the drive shaft assembly 40 may be cleaned and sterilized for a plurality of procedures such that the drive shaft assembly 40 may be used to engage different tools during different procedures without requiring additional attachments.

Figure 6:
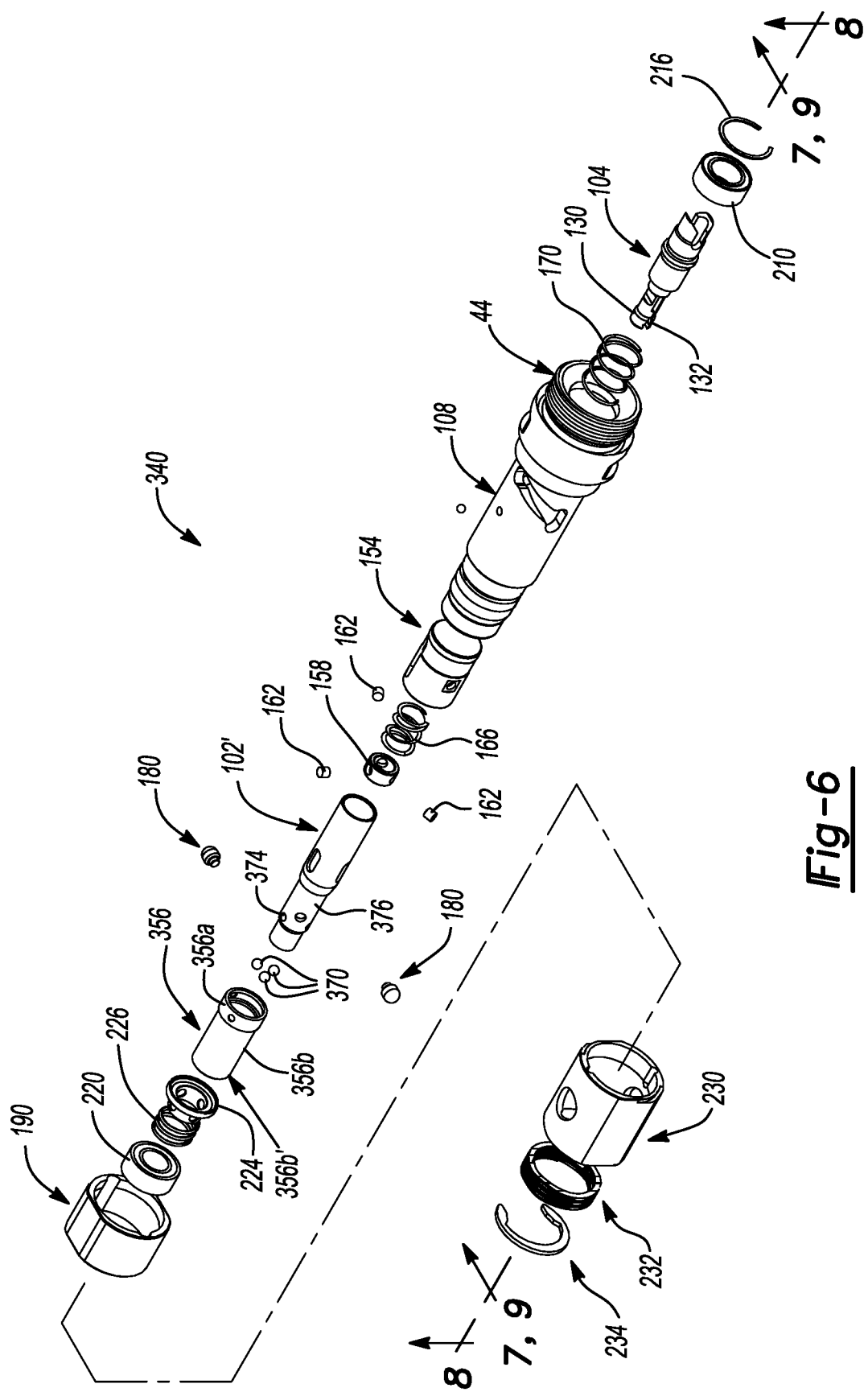
FIG. 6 is an exploded view of a drive shaft, according to various embodiments.
Figure 7:
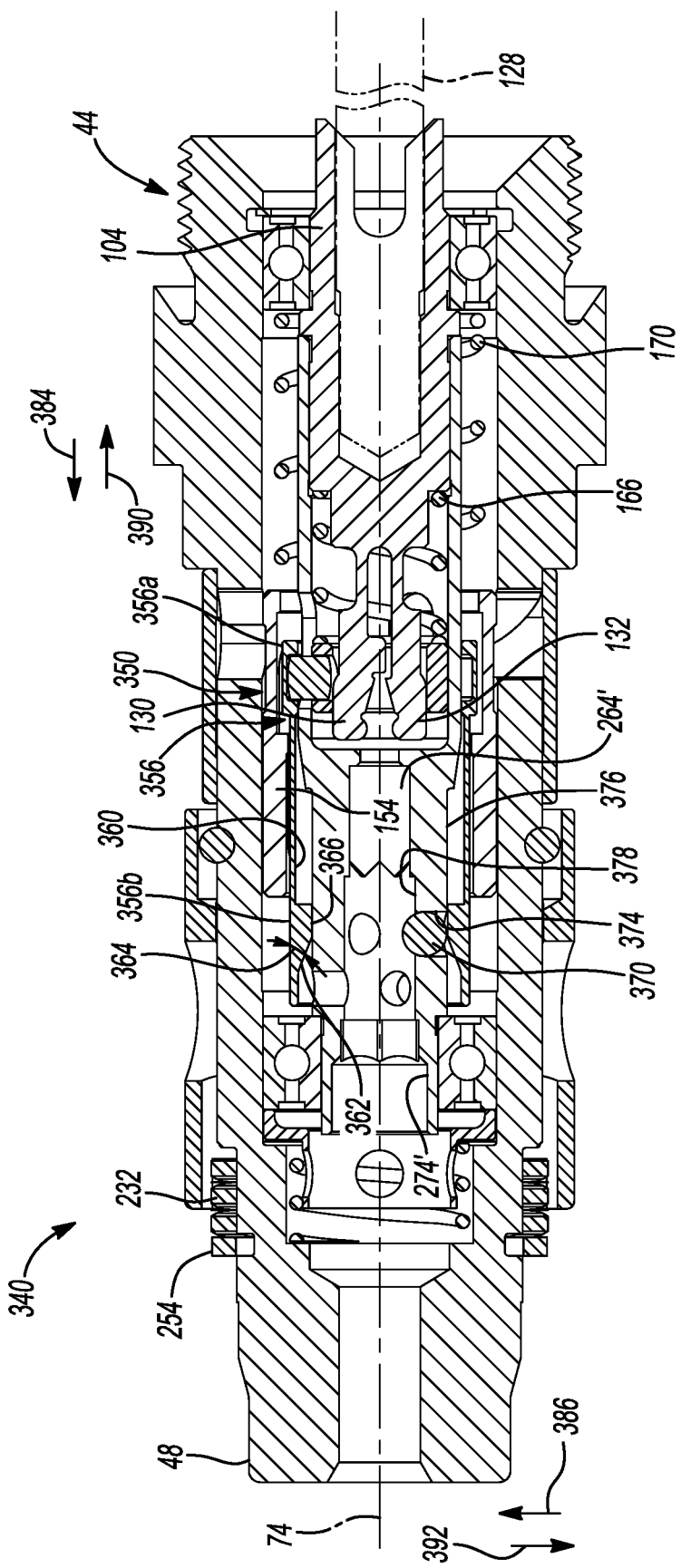
FIG. 7 is an assembled cross-sectional view of the drive shaft of FIG. of FIG. 6 along line 7-7.

With reference to FIGS. 6, 7, 8, and 9, a collet and drive shaft assembly 340 is illustrated including a drive shaft 100'. The collet and drive shaft assembly 340 may include several portions similar or identical to the collet and drive shaft assembly 40, discussed above. These portions will be referenced with the same reference numerals and will not be described in detail here. However, the collet and drive shaft assembly 340 may include portions that are augmented, replaced, or changed from the collet and drive shaft assembly 40 discussed above. The collet and drive shaft assembly 340, as illustrated in FIG. 6, may include a drive shaft 100' that includes a the first drive shaft portion 102' and the second drive shaft portion 104 including portions as discussed above. The first drive shaft portion 102' may be similar to the first drive shaft portion 102, discussed above, but augmented as described below.

The drive shaft 100' including the first portion 102' and the second drive shaft portion 104 may further include the tangs 130, 132 as discussed above. The tangs 130, 132 may be biased towards the central axis 74 with a biasing assembly 350 similar to the biasing assembly 150 discussed above. The biasing assembly 350 may include various portions including those discussed above. Further, various portions as discussed above may be augmented as discussed further herein to provide a biasing and retention mechanism for the tool, including the tool 50, 52, and 54.

The biasing assembly 350 includes the carrier 154 and an outer sleeve 356. The outer sleeve 356 may include a proximal sleeve portion 356a similar to the outer sleeve 156 positionable over the drive shaft assembly 100, discussed above. The outer sleeve 356 may further include a distal sleeve portion 356b. The distal sleeve portion 356b may include an external wall 356b' that extends from the proximal sleeve portion 356a toward the tool receiving end 48. The outer sleeve extension portion 356b may further include an internal surface 360. The internal surface 360 may further include a ramp or inclined surface 362 that extends at an angle 364 from the internal surface 360. The ramp surface 362 may extend from the internal surface 360 at the angle 364 such that a distal portion of the ramp surface 362 is closer to the internal surface 360 and a proximal portion of the ramp surface 362 is at or near a shoulder or protrusion 366. Therefore, the ramp surface 362 is extending away from the internal surface 360.

The surface 362 and the protrusion 366 may act upon a biasing or locking member 370. The biasing or locking member 370 may include a plurality of biasing or locking members, such as three biasing or locking members 370. In various embodiments, each of the locking members 370 may be provided as a substantially spherical ball. Each of the plurality of locking members 370 may be spaced apart from one another around the axis 74, such as 120 degrees apart.

Each locking member 370 may be positioned between the inner surface of the outer sleeve 356 and a respective pocket 374 formed through the first drive shaft portion 102'. The pockets 374 may include a selected geometry where the locking member 370 may extend through an outer surface 376 of the first drive shaft portion 102', but are not able to pass entirely through and fall into the internal region, such as in the third tool engaging region 274 of the first drive shaft portion 102'. For example, the pocket 374 may include a taper geometry to taper from the exterior surface 376 to an interior surface 378. Additionally, or alternatively, the pocket 374 may include a concave internal geometry having an internal diameter great enough to receive the locking member 370, but allows only a selected portion of the locking member 370 to extend into the inner surface or past the inner surface 378. For example, the geometry of the pocket 374 may be formed to allow a maximum distance, such as about 1 mm, of the locking member 370 to extend past the inner surface 378.

The locking members 370 may assist in locking or radially engaging an external surface of the tool positioned within the drive shaft 100'. For example, a shaft of the tool, such as the tool 50, may be engaged by an external surface of the locking member 370. Therefore the locking member 370 may axially lock and/or radially stabilize the tool 50 during operation of the drive shaft 100'. It is understood, however, that the locking members 370 may only radially stabilize (i.e., minimize radial movement or vibration) of the tool 50 during operation of the drive shaft 100'. As discussed herein, the locking members 370 may operably engage a selected portion of a tool to assist in axial fixation. If the tool, however, does not include an axial holding feature the locking members 370 may operate only, or substantially only, to radially stabilize the tool.

Figure 9:
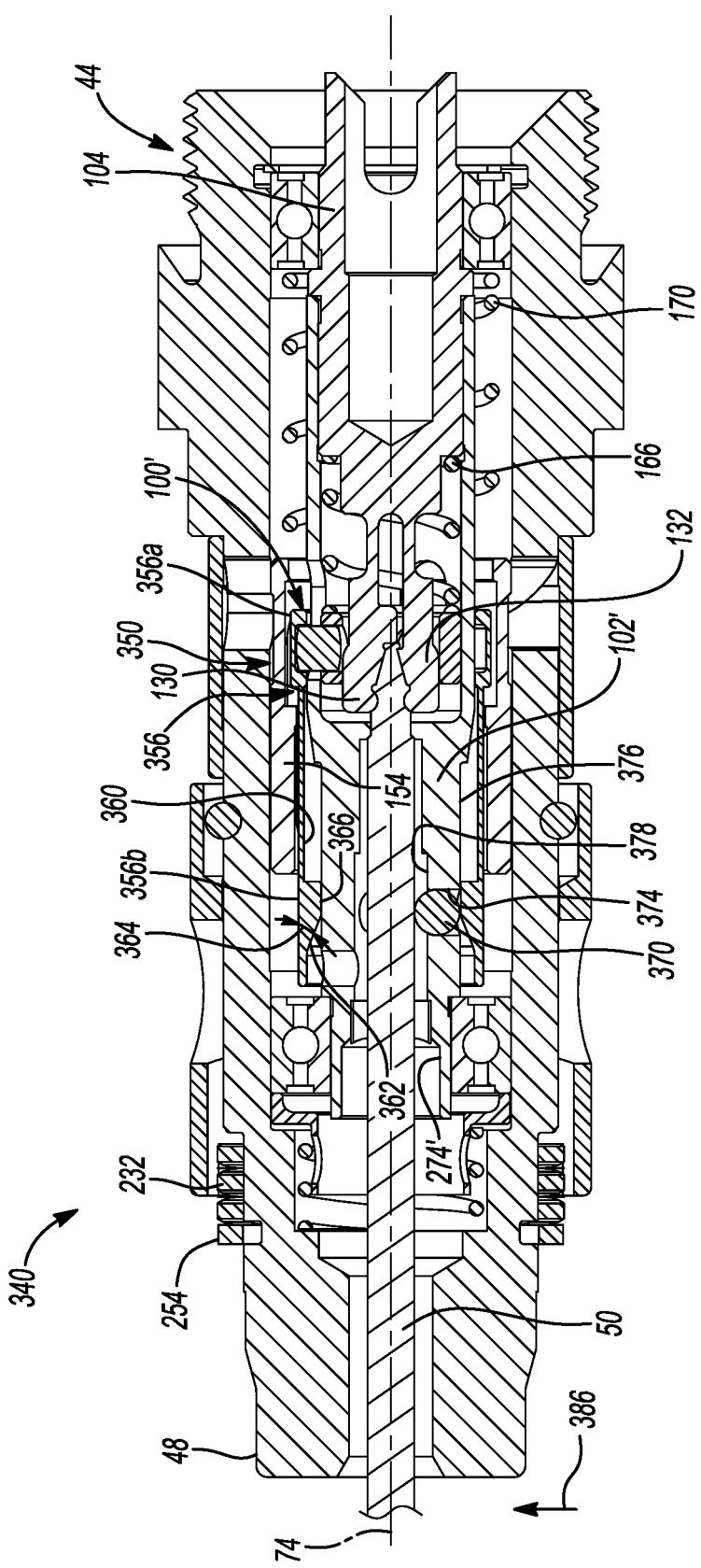
FIG. 9 is an assembled cross-sectional view of the drive shaft of FIG. 6 along line 9-9 with an instrument therein.

In operation, to lock or engage the tool 50 in the drive shaft 100', the outer sleeve 356 may be moved axially towards the tool receiving end 48 similar to movement of the outer sleeve 156, as discussed above. Movement of the outer sleeve 356 towards the tool receiving end 48 generally in the direction of arrow 384 will move the sleeve extension portion 356b such that the locking members 370 move along the ramp surface 362 towards the protrusion 366. As the locking members 370 move along the ramp surface 362, the locking members 370 move towards the axis 74 generally in the direction of arrow 386. The locking member 370 may be in contact with the external surface of the tool 50, 52, or 54 as illustrated in FIG. 9.

When disengaging the tool from the drive shaft 100, the outer sleeve 356 may be generally moved in the direction of arrow 390 similar to moving the outer sleeve 156 in the direction of arrow 194, as discussed above. Movement of the outer sleeve 356 generally in direction of arrow 390 will move the sleeve extension portion 356 in the direction of arrow 390 and allow the locking members 370 to move along the ramp surface 362 away from the central axis 74 generally in direction of arrow 392. By allowing the locking members 370 to move in the direction of arrow 392, the locking members 370 may disengage or be removed away from the external surface of the selected tool, such as the tool 50, 52, or 54. Thus, the tool may be removed from the drive shaft 100 by also having the tangs 130, 132 disengage from the selected tool along with the locking members 370.

Accordingly, the drive shaft assembly 340, as illustrated in FIGS. 6-9, may allow for an additional or secondary axial fixation and/or stabilization of a selected tool. The selected tool may be inserted into the drive shaft assembly 340 and the external sleeve 356 may be moved to bias the locking members 370 against the selected tool. The selected tool may then be removed after moving the external sleeve 356 to unbias the locking members 370 from the selected tool. Nevertheless, as discussed above, the tangs 130 and 132 may be used to engage and disengage all selected tools positioned within the drive shaft assembly 340 and the locking members 370 may be supplementary and/or auxiliary to the tangs 130, 132.

Figure 10:
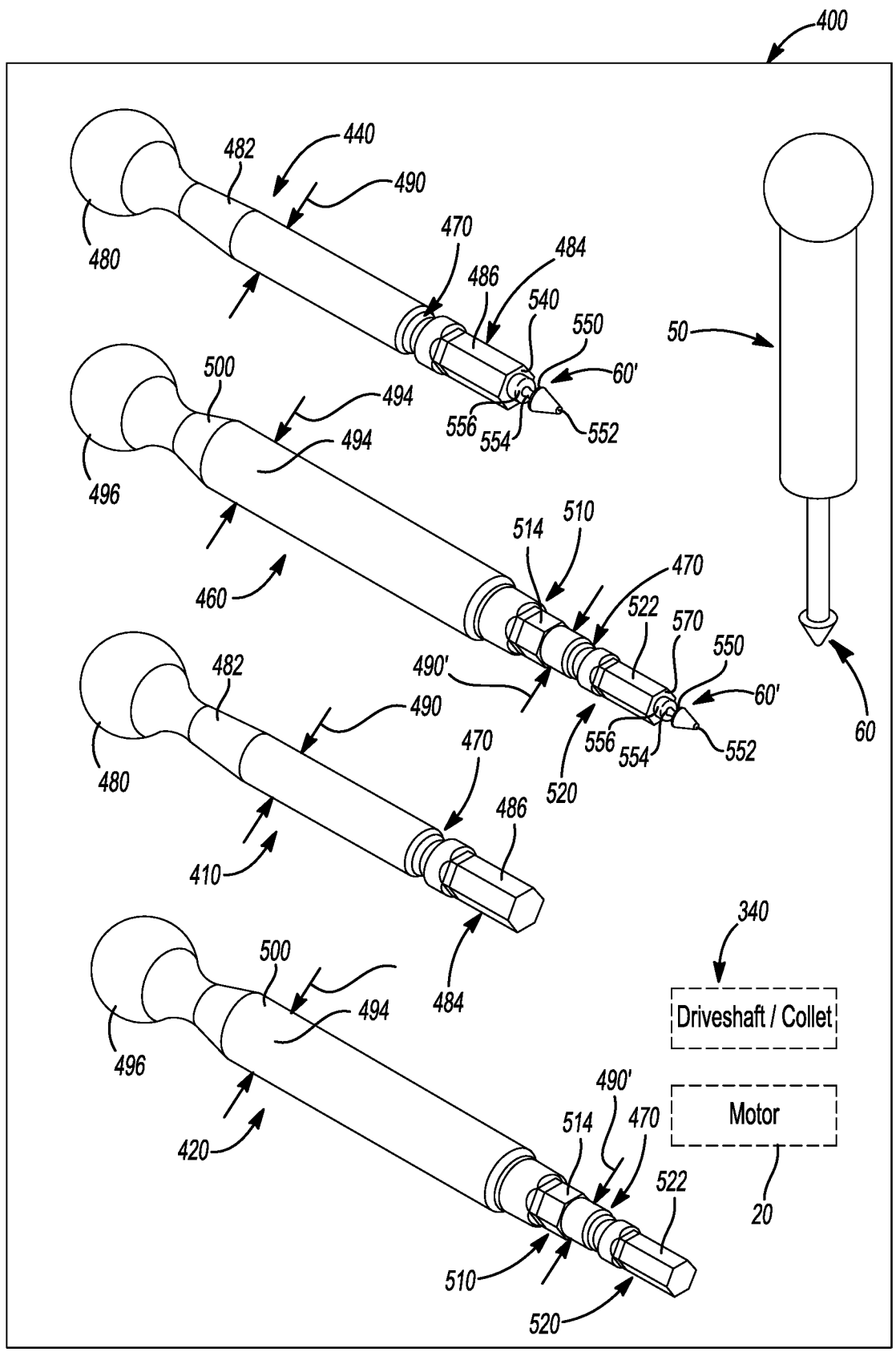
FIG. 10 is a plan view of a kit of a plurality of tools.

The collet and drive shaft assembly 340, as illustrated in FIGS. 6-9 may be operated by the drill motor 10, as discussed above, to power one or more tools. As discussed above, the collet and drive shaft assembly 340 may be used to operate the tool 52, 54, 56, which may be included in a kit, as discussed above and illustrated in FIG. 2. Further, the collet and drive shaft assembly 340 may be used to power tools included in a kit 400, as illustrated in FIG. 10. The kit 400 may include various portions, such as the collet and drive shaft assembly 340 and the motor assembly 20. It is understood, however, that the kit 400 may not include the collet and drive shaft assembly 340 and/or the motor 20, but may rather only include tools.

The kit 400 may include one or all of the tools including the first tool 52, a fourth tool 410, a fifth tool 420, a sixth tool 440, and a seventh tool 460. Each of the tools 52, 410, 420, 440, and 460 may be interconnected with the drive shaft 100' including the first driveshaft portion 102' and the second drive shaft portion 104. The various tools may include retaining features or regions. For example, the tool 52 may include the retaining region 60, as discussed above. The tools 440 and 460 may also include a retaining region 60'. The retaining region 60' may be identical to the retaining region 60 or be augmented. Regardless, the retaining region 60 and 60' may be engaged in the drive shaft 100', as discussed herein. The tool 410 and the tool 420 may include a retaining region 470 that is retained by the or engaged by the locking members 370. As discussed above, the locking members 370 may move in the direction of arrow 386 when urged and/or biased by the protrusion 360 by moving along the surface 362. The locking members 370, therefore, may engage the retaining region 470 of the tools 410 and 420. The tools 440 and 460 may also include a retaining region 470 as an auxiliary and/or supplementary retaining region 60'.

The retaining region 470 may be formed as one or more depressions. For example, the retaining region 470 may include an annular depression or groove formed around the respective tools 410, 420, 440, and 460. It is also understood that the retaining region 470 may be formed as a plurality of discrete depressions that are selected based upon the number of the locking members 370. For example, three or more depressions may be formed in an exterior surface of the respective tools 410, 420, 440, and 460 to receive or be engaged by one or more of the locking members 370 when the respective tools are positioned within the drive shaft collet assembly 340. Regardless, the retaining portion 470 may be engaged by the locking members 370 when the respective tool is positioned in the collet and drive shaft assembly 340.

Figure 8:
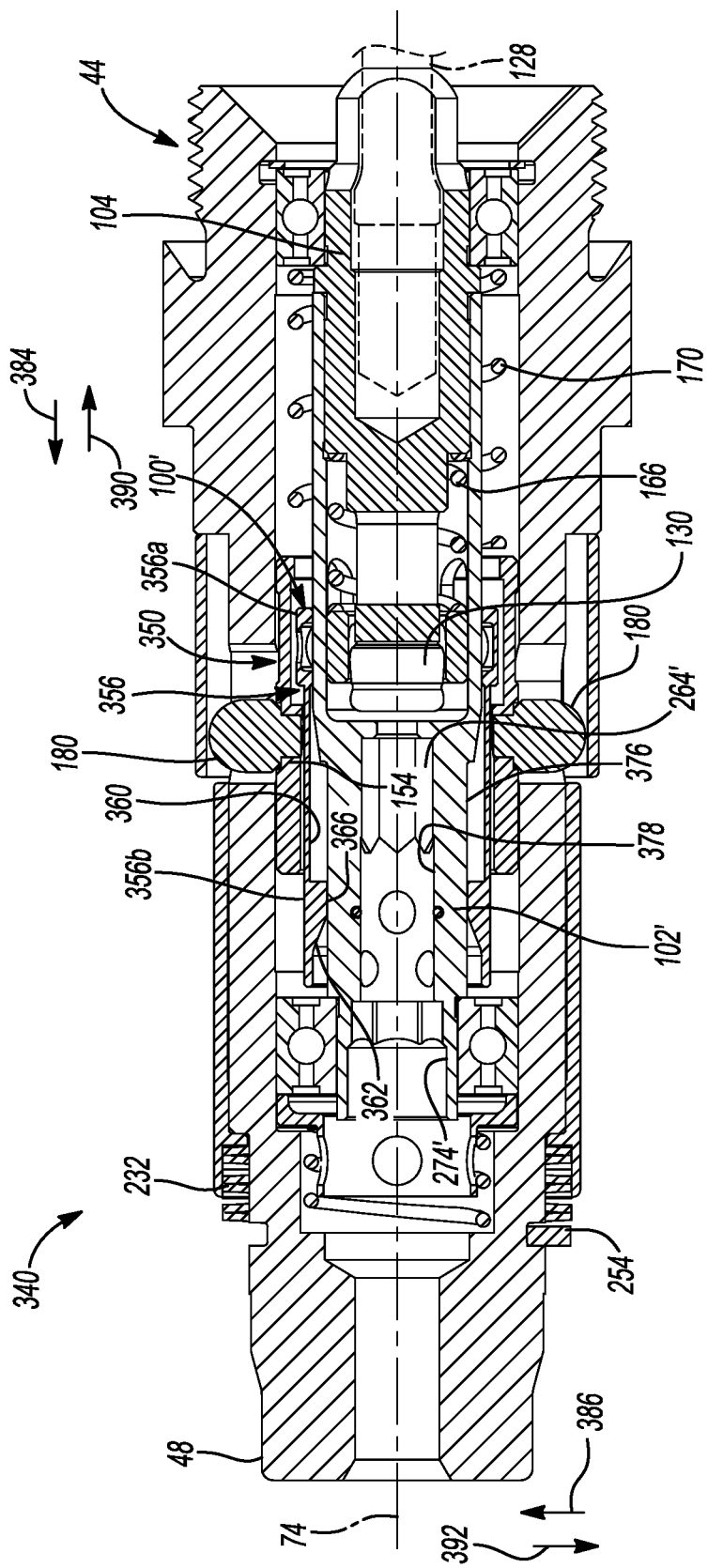
FIG. 8 is an assembled cross-sectional view of the drive shaft of FIG. 6 along line 8-8.

With initial reference to the fourth tool 410, the fourth tool 410 may include a working end 480 that may be formed as a selected working end or tool portion such as a burr, drill point, reamer, or the like. The working end 480 may extend from a shaft 482. The retaining region 470 may be formed as a depression into the shaft 482 near to a driving portion 484. The retaining portion 470 may be formed between the driving portion 484 and the working end 480. The driving portion 484 may be formed with one or more flats 486 on an external surface of the shaft 482. The flats 486 of the driving portion 484 may be received and engage the drive shaft 100' at a selected drive region or portion including a second tool driving region 264', as illustrated in FIG. 8.

The second tool driving region 264' may be substantially identical to the second tool driving region 264 discussed above and illustrated in FIG. 3. The driving portion 484 may engage the second driving portion 264' in a manner similar to that discussed above. The second tool driving region 264' may include a female receiving region that is complementary to the shape of the driving portion 484 of the tool 410. For example, the driving portion 484 of the tool 410 may include a hexagonal or pentagon cross-section and the second tool driving region 264' may include a complementary internal hexagonal or pentagon cross-section. Therefore, once the tool 410 is engaged in the second tool driving region 264', the drive shaft 100' may transfer force to the tool 410 via the tool driving portion 484.

As discussed above, the locking member 370 may be moved to engage the retaining region 470 of the tool 410 once positioned within the collet and drive shaft assembly 340. Due to the locking member 370, no other axial retaining mechanism may be necessary to retain the tool 410 within the drive shaft 100'. The drive shaft 100', therefore, may be powered by the drill motor 20 to rotate the tool 410 for a selected operation, as discussed above. The retaining region 60, however, may not be necessary to retain the tool 410 in the drive shaft assembly 100'. It is understood, however, that the tangs 130, 132 may be included in the second drive shaft portion 104 to retain a selected tool, such as the tool 50, if the first tool 50 is selected to be engaged in the drive shaft 100'.

With additional reference to FIG. 10, the fifth tool 420 may include a selected geometry that is different from the fourth tool 410. For example, the tool 410 may include a shaft diameter 490 that is less than a shaft diameter 494 of the tool 420. The tool 420, however, may also include a working end 496. The working end 496 may be different than the working end 480, such as including a different size, a different geometry, or a different type. The tool 420 further includes a shaft 500 that may include or have formed therein the retaining region 470. The retaining region 470 may be identical to the retaining region 470 of the tool 410, discussed above. Therefore, the retaining region 470 may be formed as an annular groove or plurality of depressions formed in the shaft 500. Further, the retaining region 470 may be formed on a portion of the shaft 500 that has a diameter 490' similar to the diameter 490 to be positioned at the placement of the locking members 370.

The tool 420 may also include a driving portion 510. The driving portion 510 may include one or more flats 514 that may be engaged in a third tool driving region 274' of the drive shaft 100'. The driving portion 510 may include a selected geometry that is complementary to the geometry of the third driving region 274'. For example, the driving portion 510 may include a hexagonal and pentagon cross-section and the third tool driving region 274' includes a complementary internal hexagon or pentagon.

The tool 420 may also include an alignment portion 520. The alignment portion 520 may also include one or more flats 522. The alignment portion 520 may be received in the second tool driving region 264'. Although a rotational force may be applied to the tool 420 via the alignment portion 520, the tool 420 may be substantially driven via the third tool driving region 274'. Therefore, the alignment region 520 may assist with simply initially aligning (e.g., axially or radially) the tool 420 in the second drive shaft portion 102'. As noted above, the various tool driving regions, including the driving regions 264', 274' and that formed by the tangs 130, 132 may be formed within the drive shaft 100'.

Again, the retaining region 470 may be engaged by the locking member 370, as discussed above, when the locking member 370 generally moves in the direction of arrow 386. The locking member 370 may provide the only axial retention mechanism for the tool 420 within the second drive shaft portion 102'. Therefore, the retaining region 60, 60' may not be necessary or provided on the tool 420. Nevertheless, the retaining region 470 when engaged by the locking member 370 may be axially retained within the drive shaft collet assembly 340 for operation of the tool 420 when powered by the motor assembly 20.

Figure 11:
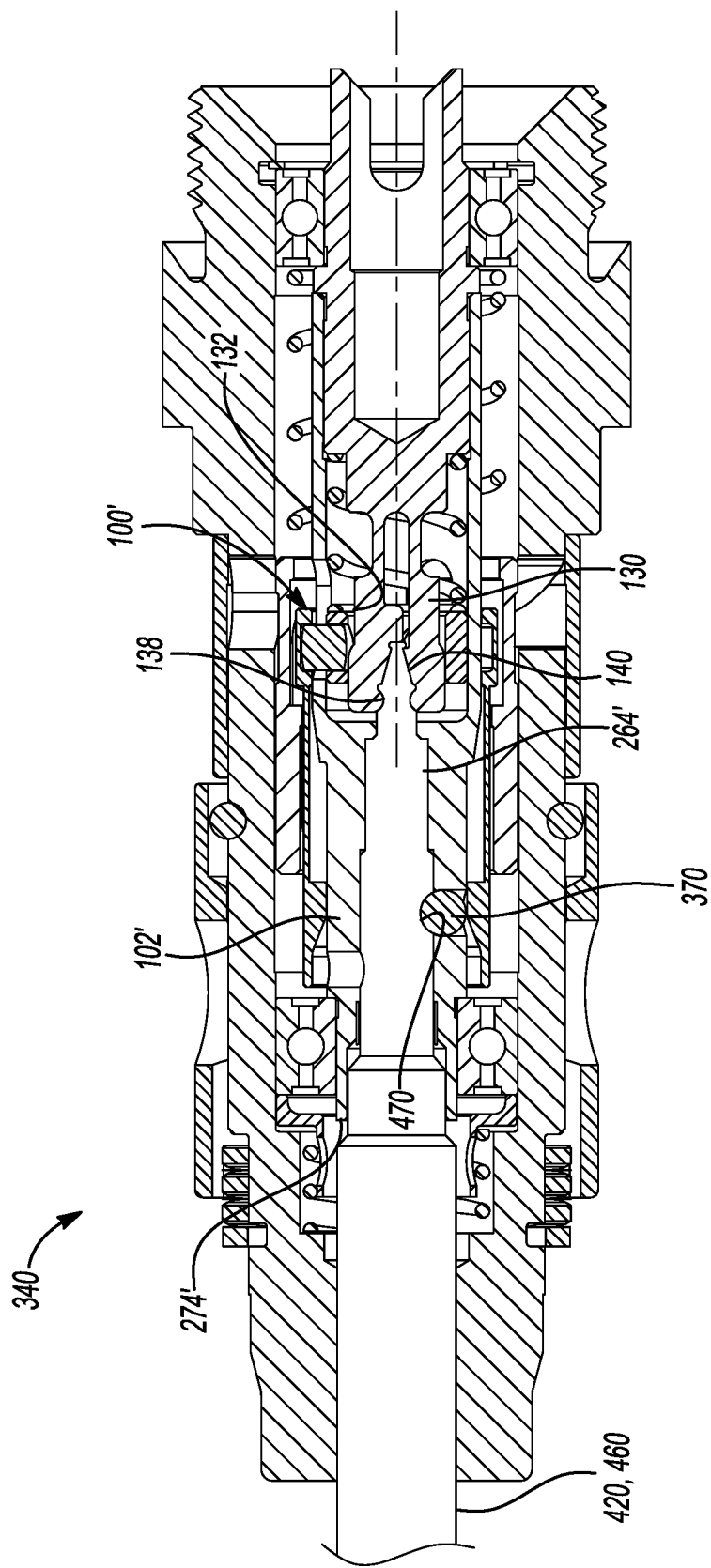
FIG. 11 is an assembled cross-section view of the drive shaft of FIG. 6 with a selected tool axially engaged therein.

With continuing reference to FIG. 10, the sixth tool 440 and the seventh tool 460 may include both the retaining portion 470 and the retaining portion 60'. The multiple retaining portions may be engaged by the collet and drive shaft assembly 340, as illustrated in FIG. 11, discussed below to assist in ensuring axial retention of the tool. It is understood, however, in various embodiments, such as with the fourth tool 410 and the fifth tool 420 that the retaining region 470 engaged with the locking members 370 may be the substantially the only axially retaining or fixing system. The driving portion may provide slight axial fixation due to frictional engagement, but generally will only provide rotational force. Further, the tools 50, 52, and 54 may include substantially only the retaining mechanism 60 as an axial fixation and retaining system when engaged via the tangs 130, 132.

With initial reference to the sixth tool 440, the tool may be similar to the fourth tool 410, discussed above. Therefore, the tool 440 may include the working end 480, the shaft 482, and the shaft diameter 490. The retaining region 470 may include an annular groove or separate depressions formed in the shaft 482, as discussed above. A tool driving portion 484 may also include one or more flats 486, as discussed above. Extending from a proximal end 540 may be the retaining region 60'. The retaining region 60' may include a distal end that may taper from a shoulder 550 to a minor diameter or cross-section at a distal tip 552. The taper portion may be generally conical. It is understood that the retaining region 60, as discussed above, need not be conical and may include one or more flat portions.

In the retaining portion 60', the shoulder 550 may be at an edge or form a portion of a depression, such as an annular groove 554 between the shoulder 550 and a second shoulder 556. The groove 554 may be engaged by the tool engaging regions 138, 140 of the tangs 130, 132, respectively. The retaining region 60' may, therefore, be engaged by the tangs 130, 132 of the second drive shaft portion 104 in a manner similar to the retaining region 60, as discussed above. The retaining region 60', however, need not be keyed to the tool engaging regions 138, 140 as the tool 440 may be driven by the first drive shaft portion 102'. This allows the tool 440 to be axially retained within the drive shaft 100' with both the retaining region 470 engaged by the locking members 370 and the retaining region 60' retained with the tangs 130, 132. The drive portion 484 may be engaged with the second tool driving region 264', as discussed above.

The seventh tool 460 may be similar to the fifth tool 420, discussed above. The tool 460, therefore, may include the working end 496 and the shaft 500. The shaft 500 may include the shaft diameter 494 as discussed above. The tool 460 may also include the tool driving region 510 having formed thereon one or more flats 514, as discussed above. The driving portion 514 may be engaged in the third driving region of 274' of the first drive shaft portion 102', as discussed above, and illustrated in FIG. 11. The second retaining region 470 may be formed as a depression, such as an annular groove 470 in the shaft 500. The retaining region 470 may be engaged by the locking members 370, as discussed above and also as illustrated in FIG. 11. Again, the retaining region 470 may be formed on a portion of the shaft 500 that has a diameter 490'. Near to the retaining region 470 may be an alignment region 520 that includes or has one or more flats 522 similar to the tool 420.

Extending from a proximal end 570 may be the retaining region 60'. The retaining region 60' may be similar to the retaining region 60' discussed above of the tool 440. Therefore, the retaining region 60' may include a shoulder 550 and a proximal region that tapers to the tip 552. The retaining region 60' may further include the second shoulder 556 and the compression, such as the annular groove 554. The retaining region 60', including the annular groove 554, allows the tool 460 to be engaged by the tangs 130, 132 with the tool engaging regions 138, 140, as discussed above.

Accordingly, with continued reference to FIG. 10 and additional reference to FIG. 11, the tool 420 is illustrated engaged in the drive shaft 100'. The retaining region 470 is engaged by the locking member 370 to axially retain the tool 420 within the drive shaft 100'. Further, as illustrated in phantom in FIG. 11, the retaining region 60' of the tool 460 is illustrated engaged by the tool engaging regions 138, 140 of the tangs 130, 132. The locking members 370 may also be engaged in the retaining region 470 of the tool 460. Therefore, the tool 460 may be retained within the drive shaft 100' with two axial retaining mechanisms. The two axial retaining mechanisms 470, 60' may be axially spaced apart. Accordingly, the sixth and seventh tools 420, 460 can be axially retained in the drive shaft 100' based upon the selected axial retaining portion 470, 60'.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A drive shaft assembly for driving at least one of a plurality of tools at different times, comprising:
    a drive shaft extending from a first end to a second end, the drive shaft including,
        a first drive shaft member forming a through bore extending through the first drive shaft member; and
        a second drive shaft member axially and rotationally fixed to the first drive shaft member within the through bore of the first drive shaft member;
    a first tool driving region formed within and by the drive shaft and configured to axially fix the plurality of tools; and
    a second tool driving region formed within and by the drive shaft and configured to engage at least a first tool of the plurality of tools; and
    wherein the second drive shaft member forms the first tool driving region and includes a first finger extending from a body of the second drive shaft member having a first flex region and a first tool engaging region and a second finger extending from the body of the second drive shaft member having a second flex region and a second tool engaging region;
    wherein the first and second flex regions are configured to flex to allow the first and second tool engaging regions to flex radially outward to engage each of the plurality of tools.

2. The drive shaft assembly of claim 1, further comprising:
    a third tool driving region formed within the drive shaft configured to engage at least a second tool of the plurality of tools.

3. The drive shaft assembly of claim 2, wherein the second tool driving region is formed as a first internal geometry having a first diameter within the through bore and the third tool driving region is formed as a second internal geometry having a second diameter within the through bore.

4. The drive shaft assembly of claim 3, wherein the second diameter is greater than the first diameter.

5. The drive shaft assembly of claim 1, further comprising:
    a biasing system biased in a first position to move at least one of the first finger or the second finger towards the other of the first finger or the second finger.

6. The drive shaft assembly of claim 5, the biasing system includes:
    an inner sleeve and a biasing spring within the through bore;
    an outer sleeve around the first drive shaft member; and a biasing pin captured between the inner sleeve and the outer sleeve;

wherein the inner sleeve, the outer sleeve and the captured biasing pin are axially moveable relative to the first drive shaft member.

7. The drive shaft assembly of claim 6, further comprising:

a carrier member moveable axially relative to the first drive shaft member, wherein the carrier member is moveable to selectively engage the outer sleeve to axially move the outer sleeve.

8. The drive shaft assembly of claim 7, further comprising:

a collet housing having a slot formed therein;

a ring configured to rotate relative to the collet housing;

a carrier pin extending through the slot and engaging the ring and the carrier member;

wherein rotation of the ring engages the carrier pin to move the carrier pin within the slot to axially move the carrier member.

9. The drive shaft assembly of claim 1, further comprising:

a biasing system biased in a first position to move at least a first locking member through an inner surface of the first drive shaft member;

wherein the locking member is configured to at least contact an exterior surface of the plurality of tools.

10. The drive shaft assembly of claim 9, wherein the locking member is configured to engage a retaining region of at least the first tool or the second tool to axially fix the first tool or the second tool within the axial portion.

11. A drive shaft assembly for driving at least one of a plurality of tools at different times, comprising:

a first drive shaft portion having a through bore extending through the first drive shaft portion;

a second drive shaft portion axially and rotationally fixed to the first drive shaft portion within the through bore of the first drive shaft portion;

a first tool driving region formed by the second drive shaft portion;

a second tool driving region formed by the first drive shaft portion;

wherein the first tool driving region is configured to axially fix a first tool;

wherein the second tool driving region is configured to rotationally engage a second tool; and wherein the second drive shaft portion forms the first tool driving region and includes a first finger extending from a body of the second drive shaft portion having a first flex region and a first tool engaging region and a second finger extending from the body of the second drive shaft portion having a second flex region and a second tool engaging region;

wherein the first and second flex regions are configured to flex to allow the first and second tool engaging regions to flex outward to engage each of the plurality of tools.

12. The drive shaft assembly of claim 11, further comprising a third tool driving region formed by the second drive shaft portion and configured to engage a third tool.

13. The drive shaft assembly of claim 12, wherein the first tool driving region is configured to axially fix the first tool, the second tool, and the third tool.

14. The drive shaft assembly of claim 13, further comprising:

a biasing system biased in a first position to move at least one of the first finger or the second finger towards the other of the first finger or the second finger.

15. The drive shaft assembly of claim 11, further comprising a secondary axial fixation system configured to provide secondary axial fixation to at least the first tool.

16. The drive shaft assembly of claim 11, wherein the second tool driving region is formed as an internal geometry within the first drive shaft portion configured to rotatably engage the second tool.

* * * * *

UNITED STATES PATENT AND TRADEMARK OFFICE
CERTIFICATE OF CORRECTION

PATENT NO. : 11,076,871 B2
APPLICATION NO. : 15/252858
DATED : August 3, 2021
INVENTOR(S) : Milton F. Barnes It is certified that error appears in the above-identified patent and that said Letters Patent is hereby corrected as shown below:

On the Title Page

Page 2, Column 2, Other Publications, Line 8, delete "Appication" and insert --Application-- therefor In the Specification Column 4, Line 32, delete "104." and insert --102.-- therefor Column 7, Line 57, delete "antoer." and insert --another.-- therefor In the Claims Column 16, Line 18, in Claim 11, after "flex", insert --radially--

Signed and Sealed this
Fourteenth Day of June, 2022

*Katherine Kelly Vidal*
*Director of the United States Patent and Trademark Office*